(12) United States Patent
Hunziker et al.

(10) Patent No.: US 9,345,436 B2
(45) Date of Patent: May 24, 2016

(54) APPARATUS AND METHODS FOR COMPUTING CARDIAC OUTPUT OF A LIVING SUBJECT

(71) Applicant: HighDim GmbH, Basel (CH)

(72) Inventors: Patrick Hunziker, Binningen (CH); Oleksii Morozov, Basel (CH); Felix Friedrich, Gattikon (CH)

(73) Assignee: HighDim GmbH (CH)

( * ) Notice: Subject to any disclaimer, the term of this patent is extended or adjusted under 35 U.S.C. 154(b) by 392 days.

(21) Appl. No.: 13/827,063

(22) Filed: Mar. 14, 2013

(65) Prior Publication Data

US 2014/0276071 A1    Sep. 18, 2014

(51) Int. Cl.
| | |
|---|---|
| *A61B 5/02* | (2006.01) |
| *A61B 5/00* | (2006.01) |
| *A61B 5/029* | (2006.01) |
| *A61B 5/021* | (2006.01) |
| *A61B 5/0452* | (2006.01) |
| *A61B 8/02* | (2006.01) |
| *A61B 8/06* | (2006.01) |
| *A61B 5/0205* | (2006.01) |
| *A61B 3/16* | (2006.01) |
| *A61B 5/024* | (2006.01) |
| *A61B 8/08* | (2006.01) |

(52) U.S. Cl.
CPC ............... *A61B 5/7278* (2013.01); *A61B 5/02* (2013.01); *A61B 5/021* (2013.01); *A61B 5/0205* (2013.01); *A61B 5/029* (2013.01); *A61B 5/02108* (2013.01); *A61B 5/0452* (2013.01); *A61B 8/02* (2013.01); *A61B 8/065* (2013.01); *A61B 8/488* (2013.01); *A61B 3/165* (2013.01); *A61B 5/024* (2013.01); *A61B 8/481* (2013.01)

(58) Field of Classification Search
CPC ...................................................... A61B 5/029
USPC ........................................ 600/300, 500, 526
See application file for complete search history.

(56) References Cited

U.S. PATENT DOCUMENTS

| | | | |
|---|---|---|---|
| 5,211,177 | A | 5/1993 | Chesney et al. |
| 6,485,431 | B1 | 11/2002 | Campbell |
| 6,705,990 | B1 * | 3/2004 | Gallant et al. ............... 600/300 |
| 7,048,691 | B2 | 5/2006 | Miele et al. |
| 7,503,896 | B2 * | 3/2009 | Miele et al. .................. 600/454 |
| 2009/0131804 | A1 | 5/2009 | Mukkamala et al. |
| 2010/0317976 | A1 | 12/2010 | Chelma et al. |
| 2011/0137183 | A1 | 6/2011 | Stok |

* cited by examiner

*Primary Examiner* — Nicole F Lavert
*Assistant Examiner* — Nadia A Mahmood
(74) *Attorney, Agent, or Firm* — Gazdzinski & Associates, PC

(57) ABSTRACT

Apparatus and methods for calculating cardiac output (CO) of a living subject. In one embodiment, the apparatus and methods build a nonlinear mathematical model to correlate physiologic source data vectors to target CO values. The source data vectors include one or more measurable or derivable parameters such as: systolic and diastolic pressure, pulse pressure, beat-to-beat interval, mean arterial pressure, maximal slope of the pressure rise during systole, the area under systolic part of the pulse pressure wave, gender (male or female), age, height and weight. The target CO values are acquired using various methods, across a plurality of individuals. Multidimensional nonlinear optimization is then used to find a mathematical model which transforms the source data to the target CO data. The model is then applied to an individual by acquiring physiologic data for the individual and applying the model to the collected data.

13 Claims, 5 Drawing Sheets

US 9,345,436 B2

APPARATUS AND METHODS FOR COMPUTING CARDIAC OUTPUT OF A LIVING SUBJECT

RELATED APPLICATIONS

This application is related to co-owned, co-pending U.S. patent application Ser. No. 13/827,063 entitled "APPARATUS AND METHODS FOR COMPUTING CARDIAC OUTPUT OF A LIVING SUBJECT VIA APPLANATION TONOMETRY", filed concurrently herewith on Mar. 14, 2013, and incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

1. Field of the Disclosure

This disclosure relates generally to methods and apparatus for measuring cardiac output of a living subject, and specifically in one aspect to using substantially non-invasive techniques to accurately estimate cardiac output of a living subject.

2. Description of Related Technology

Cardiac output (CO) refers to the volume of blood pumped by the heart (by a left or right ventricle) over a period of time, such as in one minute. CO may further refer to the combined sum of output from the right ventricle and the output from the left ventricle during the phase of systole of the heart, and is mathematically expressed as:

$$CO = \text{Stroke Volume} \times \text{Heart Rate}$$

Heart rate (HR) refers to the number of heartbeats per unit of time, typically measured as beats per minute (bpm). Stroke volume (SV) refers to the volume of blood pumped from one ventricle of the heart with each beat.

Heart functioning and CO are generally controlled by the demand for oxygen by the body's cells. As the oxygen demand increases, CO increases. Therefore, increases in HR, change of posture, increased sympathetic nervous system activity, and decreased parasympathetic nervous system activity, body surface area, etc. may affect a patient's CO. Other physiologic parameters and measures may further affect SV and/or HR, and therefore also affect CO. For example, the Ejection Fraction (EF), which is the fraction of blood ejected by the Left Ventricle (LV) during the contraction or ejection phase of the cardiac cycle or systole, may affect SV and may vary with ventricular disease associated with ventricular dilatation. Other diseases of the cardiovascular system cause changes to CO, such as hypertension and heart failure. In addition, during infection and sepsis CO may increase, and as a result of cardiomyopathy and heart failure, CO may decrease. CO can also be affected significantly by the phase of respiration (i.e., intra-thoracic pressure changes influence diastolic filling and therefore influence CO). CO changes are especially important and efficient techniques for monitoring CO and are therefore needed during mechanical ventilation as well.

Hence, the ability to accurately measure CO is important for providing improved diagnosis of abnormalities and management thereof, including hypertension, heart failure, etc.

There are a number of clinical methods for measurement of CO, ranging from direct intracardiac catheterisation to non-invasive measurement of the arterial pulse. However, each of these methods has significant limitations including inaccuracy, ineffectiveness, and invasiveness. Specifically, pathophysiologic studies indicate that left ventricular systolic and diastolic function, as well as central vascular function, are nonlinear processes. Therefore, computation of cardiac output using the prior art linear approximation strategies is imprecise and suboptimal. Accordingly, there exists no widely accepted standard for truly accurate measurement of CO.

Hence, what are needed are accurate, effective, and non-invasive apparatus and methods for calculating CO.

SUMMARY

The present disclosure addresses the foregoing needs by disclosing, inter alia, apparatus and methods for computing cardiac output of a living subject via a tonometric device.

In a first aspect, a method for computing cardiac output from applanation tonometry data is disclosed. In one embodiment, the method comprises obtaining actual hemodynamic parameter values from applanation tonometry, applying the mathematical model, and causing the display of a cardiac output value.

In a second aspect, a cardiac output device is disclosed. In one embodiment, the device comprises at least one interface, at least one storage apparatus, a processor and an external component to measure hemodynamic parameter from applanation tonometry. In one variant, the processor is configured to run at least one computer program for pre-processing measured hemodynamic parameter data. In another variant, the processor is configured to run at least one computer program for calculating cardiac output.

In a third aspect, a non-transitory computer readable medium configured to store a computer program thereon is disclosed. In one embodiment, the computer program comprises a plurality of instructions configured to calculate cardiac output. In one variant the plurality of instructions are configured to when executed by a processor: measure a plurality of hemodynamic parameters, process the measured hemodynamic parameter data, select an input vector based at least in part on the measured plurality of hemodynamic parameters, apply a mathematical model for computing cardiac output, and cause the display of a calculated cardiac output value.

In a fourth aspect, a method for computing cardiac output is disclosed. In one embodiment, the method comprises obtaining target values for cardiac output given an input hemodynamic parameter vector, building a mathematical model, obtaining actual hemodynamic parameter values, applying the mathematical model, and causing the display of a cardiac output value.

In a fifth aspect, a method of generating a mathematical model for use in computing cardiac output is disclosed. In one embodiment, the method comprises measuring a plurality of physiologic parameter values, generating a plurality of input vectors based at least in part on the physiologic parameter values, collecting a plurality of cardiac output measurements, using the collected cardiac output measurements and the physiologic parameter values to compute target cardiac output values, and using a non-linear optimization algorithm to generate the mathematical model for use in computing cardiac output.

In a sixth aspect, a method of computing cardiac output is disclosed. In one embodiment, the method comprises measuring a plurality of hemodynamic parameters, processing the measured hemodynamic parameter data, selecting an input vector based at least in part on the measured plurality of hemodynamic parameters, applying a mathematical model for computing cardiac output, and causing the display of a calculated cardiac output value.

In a seventh aspect, a cardiac output device is disclosed. In one embodiment, the device comprises at least one interface, at least one storage apparatus, and a processor. In one variant, the processor is configured to run at least one computer program for generating a mathematical model for use in computing cardiac output. In another variant, the processor is configured to run at least one computer program for pre-processing measured hemodynamic parameter data. In another variant, the processor is configured to run at least one computer program for generating a plurality of hemodynamic parameter vectors. In yet another variant, the processor is configured to run at least one computer program for calculating cardiac output.

In a eighth aspect, a non-transitory computer readable medium configured to store a computer program thereon is disclosed. In one embodiment, the computer program comprises a plurality of instructions configured to calculate cardiac output. In one variant the plurality of instructions are configured to when executed by a processor: obtain target values for cardiac output given an input hemodynamic parameter vector, build a mathematical model, obtain actual hemodynamic parameter values, apply the mathematical model, and cause the display of a cardiac output value.

In a ninth aspect, a non-transitory computer readable medium configured to store a computer program thereon is disclosed. In one embodiment, the computer program comprises a plurality of instructions configured to generate a mathematical model for use in computing cardiac output. In one variant, the plurality of instructions are configured to when executed by a processor: measure a plurality of physiologic parameter values, generate a plurality of input vectors based at least in part on the physiologic parameter values, collect a plurality of cardiac output measurements, use the collected cardiac output measurements and the physiologic parameter values to compute target cardiac output values, and use a non-linear optimization algorithm to generate the mathematical model for use in computing cardiac output.

In a tenth aspect, a non-transitory computer readable medium configured to store a computer program thereon is disclosed. In one embodiment, the computer program comprises a plurality of instructions configured to calculate cardiac output. In one variant the plurality of instructions are configured to when executed by a processor: measure a plurality of hemodynamic parameters, process the measured hemodynamic parameter data, select an input vector based at least in part on the measured plurality of hemodynamic parameters, apply a mathematical model for computing cardiac output, and cause the display of a calculated cardiac output value.

These and other features of the disclosure will become apparent from the following description, taken in conjunction with the accompanying drawings.

DETAILED DESCRIPTION

Figure 1:
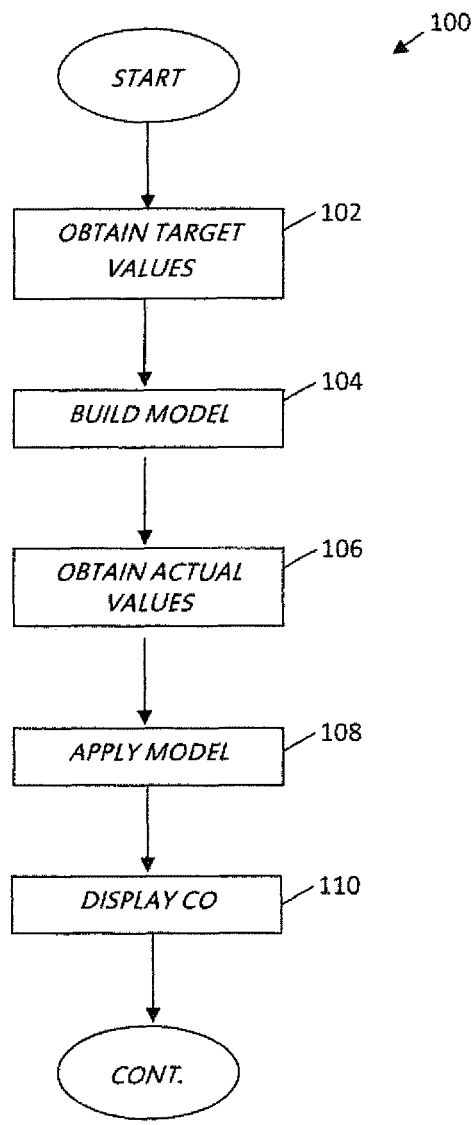
FIG. 1 is a flow diagram illustrating one embodiment of a generalized method for calculating cardiac output according to the present disclosure.

Reference is now made to the drawings wherein like numerals refer to like parts throughout.

It is noted that while the disclosure is described herein primarily in terms of an apparatus and methods calculating cardiac output of a living subject utilizing measurements of hemodynamic parameters obtained either in invasive or non-invasive way such as blood pressure obtained via the radial artery (i.e., wrist) of a human subject using applanation tonometry, the disclosure may also be readily embodied or adapted to utilize such parameters at other blood vessels and locations on the human body, as well as utilizing these parameters on other warm-blooded species. Similarly, the techniques of the present disclosure can be utilized with respect to other parameter measurements, as well as within other similar fluidic systems which have similar properties to those of the circulatory system of a living being. All such adaptations and alternate embodiments are readily implemented by those of ordinary skill in the relevant arts, and are considered to fall within the scope of the claims appended hereto.

As used herein, the term "continuous" is meant to include without limitation continuous, piece-wise continuous, and/or substantially continuous processes (e.g., those which are generally continuous in nature, but are not per se continuous).

As used herein, the term "hemodynamic parameter" is meant to include parameters associated with the circulatory system of the subject, including for example pressure (e.g., diastolic, systolic, pulse, or mean pressure), derivatives or combinations thereof, arterial flow, arterial wall diameter (and its derivatives), cross sectional area of the artery, and arterial compliance.

Additionally, it is noted that the terms "tonometric," "tonometer," and "tonometry" as used herein are intended to broadly refer to non-invasive surface measurement of one or more hemodynamic parameters, such as by placing a sensor in communication with the surface of the skin, although contact with the skin need not be direct, and can be indirect (e.g., such as through a coupling medium or other interface).

As used herein, the term "application" (in the context of a software application) refers generally to a unit of executable software that implements a certain functionality or theme. The themes of applications vary broadly across any number of disciplines and functions (such as on-demand content management, e-commerce transactions, brokerage transactions, home entertainment, calculator etc.), and one application may have more than one theme. The unit of executable software generally runs in a predetermined environment; for example, the unit could comprise a downloadable Java Xlet™ that runs within the JavaTV™ environment.

As used herein, the term "computer program" or "software" is meant to include any sequence or human or machine cognizable steps which perform a function. Such program may be rendered in virtually any programming language or environment including, for example, C/C++, Fortran, COBOL, PASCAL, assembly language, markup languages (e.g., HTML, SGML, XML, VoXML), and the like, as well as object-oriented environments such as the Common Object Request Broker Architecture (CORBA), Java™ (including J2ME, Java Beans, etc.) and the like.

As used herein, the terms processor, "microprocessor" and "digital processor" are meant generally to include all types of digital processing devices including, without limitation, digital signal processors (DSPs), reduced instruction set computers (RISC), general-purpose (CISC) processors, microprocessors, gate arrays (e.g., FPGAs), PLDs, reconfigurable compute fabrics (RCFs), array processors, and application-specific integrated circuits (ASICs). Such digital processors may be contained on a single unitary IC die, or distributed across multiple components.

Overview

In one fundamental aspect, the present disclosure comprises apparatus and methods for calculating cardiac output. In one embodiment, the concepts of artificial intelligence and machine learning are used to perform multidimensional non-linear optimization with the goal to build a nonlinear mathematical model for cardiac output that overcomes the limitation of conventional linear approaches. The mathematical model links, in a mathematically optimal way, physiologic input source data vectors to target cardiac output values measured beat-by-beat or as short-term mean values corresponding to a moving average over a pre-specified time.

The physiologic input data is collected via measurements produced by a hemodynamic sensor or other equipment, or may be derived from data produced by the sensor. The measured parameters include e.g., a) systolic pressure, b) diastolic pressure, c) pulse pressure, d) beat-to-beat interval, e) mean arterial pressure, f) maximal slope of the pressure rise during systole, g) the area under systolic part of the pulse pressure wave. These measurements are combined with gender (male or female), age, height and weight as an additional set of input parameters passed to a chosen non-linear model.

The target cardiac output values are obtained using the mathematical concept of regression to the mean, which implies that application of multiple measurement modalities leads to minimization of systematic bias components associated with individual methods, and that oversampling leads to minimization of the statistical noise. Therefore, cardiac output values are acquired in one implementation using a number of methods, including established waveform-based methods, Doppler echocardiography-based, and thermodilution-based, across a plurality of individuals.

Multidimensional nonlinear optimization is then used to find a mathematical model which transforms the physiologic input data into the target cardiac output data in a least-square optimal fashion.

The model is then applied to an individual patient.

Example Operation

As discussed above, cardiac output (CO) refers to the combined sum of output from the right ventricle and the output from the left ventricle during the phase of systole of the heart, and is mathematically expressed as:

CO=Stroke Volume×Heart Rate where heart rate (HR) refers to the number of heartbeats per unit of time (in bpm), and stroke volume (SV) refers to the volume of blood pumped from one ventricle of the heart with each beat (in mL).

As previously noted, pathophysiologic studies indicate that left ventricular systolic and diastolic function, as well as central vascular function, are non-linear processes. Therefore, computation of cardiac output using the prior art linear approximation strategies is imprecise and suboptimal. Hence, the present disclosure improves on the current technologies by providing, inter alia, a non-linear based mechanism for calculating CO.

Referring now to FIG. 1, a generalized method 100 for calculating cardiac output according to the present disclosure is illustrated. As shown, the method generally comprises obtaining a plurality of target values for cardiac output (step 102). As will be discussed in greater detail below with respect to FIG. 2, the target values are in the exemplary embodiment obtained from CO measurements by Doppler, thermodilution etc. and using regression to the mean. A non-linear optimization algorithm is used to build a mathematical model capable of estimating CO based on one or more measured physiologic parameters of a living subject.

At step 104, a mathematical model is built. The mathematical model (as illustrated in Appendices I and II) is configured to link one or more measured hemodynamic parameters to a target CO value. Thus, per step 106, one or more hemodynamic parameters of the subject are measured. The hemodynamic parameters may be measured using with literally any type of apparatus adapted for hemodynamic parameter measurement. The hemodynamic parameters are measured using applanation tonometry including for example via the devices described in co-owned U.S. Pat. No. 7,503,896 entitled "METHOD AND APPARATUS FOR THE NONINVASIVE ASSESSMENT OF HEMODYNAMIC PARAMETERS INCLUDING BLOOD VESSEL LOCATION" issued on Mar. 17, 2009, and U.S. Pat. No. 7,048,691 entitled "METHOD AND APPARATUS FOR ASSESSING HEMODYNAMIC PARAMETERS WITHIN THE CIRCULATORY SYSTEM OF A LIVING SUBJECT" issued May 23, 2006, both of which are assigned to the assignee hereof and incorporated herein by reference in their entirety. Other apparatus for each of the hemodynamic parameter measurements disclosed herein may be used in addition to (or in place of) the apparatus and methods described in the cited co-owned patents and patent applications.

Per step 108 of the method 100, the mathematical model (built at step 104) is applied to the hemodynamic parameter values obtained at step 106. As noted above, the mathematical model links the measured hemodynamic parameters to a target CO value. Therefore, when it is applied in step 108, the model is able to approximate a CO value given the measured hemodynamic parameters. This CO value is then displayed to a user (step 110) or used as an input to another device or process.

Generating an Optimized Mathematical Model for Calculating Cardiac Output

Figure 2:
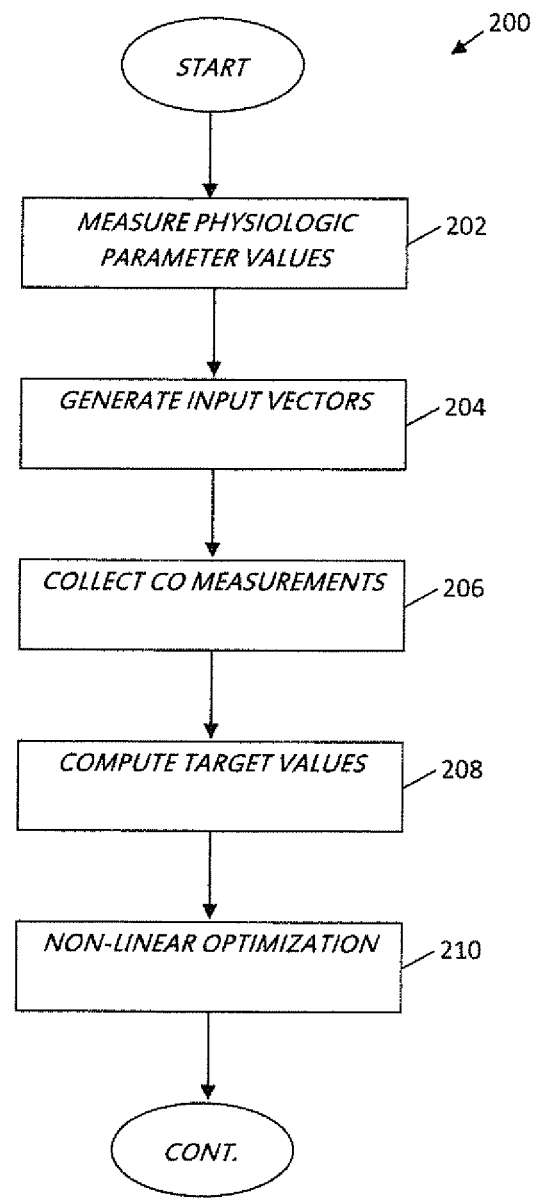
FIG. 2 is a flow diagram illustrating one embodiment of a generalized method for generating an mathematical model for calculating cardiac output according to the present disclosure.

Referring now to FIG. 2, an exemplary embodiment of a general method 200 for generating a mathematical model which is used to calculate CO is illustrated.

The method 200 generates the mathematical model by utilizing data collected from a sample of living subjects (i.e., test subjects), the size of the sample population being ideally large. Per step 202, a plurality of physiologic parameter values are measured for each of the subjects. The measured physiologic parameters may include for example the subject's height (such as in cm) and weight (such as in kg), which are measured using traditional tools for doing so.

Additionally, the measured physiological parameters include systolic blood pressure (PSys; in mmHg) and diastolic blood pressure (PDia; in mmHg), which may be measured for example via an auscultatory method using an aneroid sphygmomanometer and a stethoscope. Alternatively, or in addition, systolic and diastolic blood pressure may be measured using e.g., the previously referenced methods and apparatus of U.S. Pat. Nos. 7,503,896 and 7,048,691, which are incorporated herein by reference in their entirety. A so-called "A-line" may also be used; however, this is less preferred as it involves an invasive procedure.

Additionally, a beat-to-beat interval (BTBI) may be among the measured physiologic parameters. The BTBI is measured by listening to each subject's heartbeat detecting a first heartbeat, and measuring (in seconds) the time to the next heartbeat. Alternatively, the BTBI may be derived from data obtained using the parameteric measurement devices previously described.

Next, per step 204 of the method, an input vector x is generated for each of the subjects. The input vectors represent a matrix of all the measured parameters (e.g., height, weight, systolic pressure (PSys), diastolic pressure (PDia), and beat-to-beat interval (BTBI)); a vector is created for each subject measured.

Additionally, the vectors may contain information which is either entered manually or derived from other measurable information. For example, the input vector may further include an age and gender of the subject, which are manually entered. Further, the input vector may include a value for pulse pressure (PP, measured in mmHg), a mean arterial pressure (MAP, in mmHg/s), a maximal slope within a systole (dPdtMax, measured in mmHg/s), and a systolic area (SysA, measured in mmHg*s). An exemplary matrix representative of the input vector is illustrated below:

$$x = [\text{Gender}, \text{Age}, \text{Height}, \text{Weight}, \text{PSys}, \text{PDia}, \text{PP}, \text{BTBI}, \text{MAP}, \text{dPdtMax}, \text{SysA}]^T$$

Derivation of the values for PP, MAP, dPdtMax, and SysA may be performed by a first process which may be running on the same processor as the process for generating the input vectors, or at a different processing entity. For example, the CO algorithm derivation device (discussed below with respect to FIG. 4) may be utilized to perform the input vector generation. The CO algorithm derivation device may also perform the mathematical operations necessary to derive the values of PP, MAP, dPdtMax, and SysA. Various other implementations will be recognized by those of ordinary skill given the present disclosure.

Pulse pressure may be derived from the difference between the systolic and diastolic blood pressure measurements. The methods and apparatus disclosed in the previously referenced U.S. Pat. Nos. 7,503,896 and 7,048,691, which are incorporated herein by reference in their entirety, may be further used to independently calculate and display PP based on systolic and diastolic blood pressure measurements.

The mean arterial pressure (MAP) is the average blood pressure in an individual, and is defined as the average arterial pressure during a single cardiac cycle. The MAP is may be calculated based on the measured value of the systolic blood pressure (PSys) and diastolic blood pressure (PDia) as follows:

$$MAP \cong \frac{(2 \times PDia) + PSys}{3}$$

The maximal slope within a systole (dPdtMax) is defined as the maximum value of the first order derivative of the blood pressure (BP) signal within the time interval corresponding to systole. It is calculated as follows:

$$dPdtMax = \max_{t \in T_{sys}} \left( \frac{dP(t)}{dt} \right)$$

where P(t) represents the BP signal and $T_{sys}$ represents the systolic interval of the current beat. In a case of a uniformly discretized BP signal, the derivative may be approximated by the first order finite difference:

$$\frac{dP(t)}{dt} \approx \frac{P(t+dt) - P(t)}{dt}$$

where dt is the sampling period of the BP signal in seconds.

Using this estimation, the dPdtMax is computed by: (i) determining the onset of the current BP beat ($t_{onset}$), (ii) determining the location of the systolic peak of the current BP beat ($t_{sys}$), (iii) computing the first order finite difference of the BP signal within the interval [$t_{onset}$, $t_{sys}$] according to the estimation given above, and (iv) determining dPdtMax as the maximum value of the computed finite difference within the interval [$t_{onset}$, $t_{sys}$].

In one embodiment, the impact of noise on the estimation of the derivative is decreased by preprocessing the BP signal using a low-pass preconditioning filter. For example, a second order Buterworth low pass filter with a cut-off frequency of 30 Hz may be used.

The systolic area (SysA) is computed according to the following equation:

$$SysA = \int_{onset}^{onset+LVET} (bp - bp_{onset}) dt$$

where an estimation of left ventricular ejection time (LVET) is computed as:

$$LVET = 0.3\sqrt{BTBI}$$

Once the foregoing values are derived, they are also placed within respective input vectors (step 204). An input vector is therefore created for each member of the (large) sample of living subjects.

Per step 206, cardiac output measurements are collected via two or more methods for each subject in the sample. In other words, for a single subject, multiple cardiac output values are obtained, each from a different method of measuring cardiac output. One or more of the following methods may be utilized to obtain CO values.

A CO value may be determined by using e.g., the Fick Principle. The Fick principle is based on the idea that the rate at which oxygen is consumed is a function of the rate of blood flow, and the rate at which oxygen is picked up by red blood cells. To calculate CO using Fick, a measurement of the oxygen consumed over a given period of time from measurement of the oxygen concentration of the venous blood and the arterial blood is utilized. To calculate CO, (i) the volume of oxygen consumed per minute ($V_{O2}$) is measured using e.g., a spirometer and a carbon dioxide absorber, (ii) the oxygen content of blood taken from the pulmonary artery (i.e., venous blood; $C_v$) is measured, and (iii) the oxygen content of blood taken from a cannula in a peripheral artery (i.e., arterial blood; $C_A$) is measured. The measurements are then used to determine CO as follows:

$$CO = V_{O2}/(C_A - C_V) * 100$$

CO may also be determined using dilution methods. To measure CO using dilution, the amount of an indicator injected into a patient's blood stream is divided by its average concentration in the arterial blood after a single circulation through the heart. The indicator may comprise a dye, and the concentration of the dye is measured at different points in the circulation, such as via an intravenous injection and then at a downstream sampling site, usually in a systemic artery. The CO may be measured as follows:

$$CO = \frac{\text{Quantity of Indicator}}{\int_0^\infty \text{Concentration of Indicator} \cdot dt}$$

Another method of calculating CO utilizes pulmonary artery thermodilution (or trans-right-heart thermodilution), which is similar to the dilution method discussed above, but replaces the indicator dye with a cooled or heated fluid. In this manner, the temperature change may be measured at different sites in the circulation (as opposed to dye concentration discussed above).

A "Doppler ultrasound" may also be utilized to measure CO, the Doppler ultrasound utilizes ultrasound and the Doppler effect. A Doppler shift in the frequency of ultrasound waves caused by the blood velocity within the heart is used to calculate flow velocity and volume, and therefore CO as follows:

$$CO = vti \times CSA \times \text{Heart Rate}$$

where CSA refers to the valve orifice cross sectional area (which is calculated using $\pi r^2$, where r refers to the valve radius), and vti refers to the velocity time integral of the trace of the Doppler flow profile.

Yet another mechanism for calculating CO utilizes echocardiography. According to this method, two dimensional (2D) imaging is used to measure the diameter (d) of the aortic annulous and therefore allow calculation of the cross-sectional area thereof. Then, using the equation listed above, the CO may be calculated by multiplying the cross-sectional area by the velocity time integral of a Doppler flow profile (vti) across the aortic valve, and by the heart rate.

Other methods for CO calculation include e.g., the transcutaneous Doppler mechanism. One exemplary device which may be utilized for making transcutaneous Doppler measurements is the so-called Ultrasonic Cardiac Output Monitor (USCOM) produced by Uscom Ltd, Sydney, Australia. Transcutaneous Doppler mechanisms use Continuous Wave (CW) Doppler to measure the Doppler flow profile (vti), and use anthropometry to calculate aortic and pulmonary valve diameters and the valve orifice cross sectional area. The use of anthropometry enables both right and left sided CO measurements.

Additionally, transesophageal Doppler (TOD) may be used to calculate CO. The TOD mechanisms utilize a CW sensor on the end of a probe which is introduced into the patient (such as via the mouth or nose) and positioned in the esophagus. The Doppler beam aligns with the descending thoracic aorta (DTA) at a known angle, and because the transducer is close to the blood flow, the signal is clear. It is noted, however, that TOD only measures DTA flow, and not true CO and requires patient sedation. Furthermore, DTA flow and therefore TOD measurements may be influenced or affected by disproportionate changes in blood flow between upper and lower body.

Pulse pressure methods may also be utilized to derive a waveform of the pressure in an artery over time, the waveform may then be utilized to calculate cardiac performance. However, such measurements include changes in pressure associated with changes in arterial function (compliance, impedance, etc.), and therefore may be unreliable. In other words, pulse pressure methods measure the combined performance of the heart and the vessels but may be imprecise for specifically measuring CO. Appropriate compensation is made via beat-to-beat calibration of the waveform to another CO measurement method. Pulse pressure may be measured invasively (such as by inserting a pressure sensor or "A-line" into the artery) and non-invasively (such as by sphygmomanometry and tonometry).

With respect to the non-invasive PP methods for measuring CO, a cuff blood pressure device (sphygmomanometer) is used to non-invasively measure blood pressure and provide common PP waveform values of systolic and diastolic pressure. The waveform values are then used to calculate PP. The PP is an indicator of heart function and/or CO, however, to fully appreciate the CO value, one must additionally take into account the elasticity of the arterial bed. In other words, the more stretched the aorta, the greater the pulse pressure. Generally, each additional 2 ml of blood results in a 1 mmHg rise in pressure. Hence, CO may be calculated as follows:

$$CO = 2 \text{ mL} \times PP \times HR$$

One or more of the previously identified tonometric apparatus of the Assignee hereof may be utilized for continuous, non-invasive pressure sensing according to this embodiment.

Cardiac output may also be measured using impedance cardiography. Impedance cardiography (ICG) measures changes in impedance across the thoracic region over the cardiac cycle invasive or non-invasively. Lower impedance indicates greater intrathoracic fluid volume and blood flow. When fluid volume changes are synchronized with heartbeat, the change in impedance can be used to calculate e.g., stroke volume, cardiac output, and systemic vascular resistance. Exemplary apparatus for measuring CO using non-invasive ICG methods include the so-called Bio-Z Dx device produced by Sonosite Inc., Bothell, Wash. and the so-called niccomo device produced by medis GmbH, Ilmenau, Germany.

In addition, ultrasound dilution (UD) may be used to measure cardiac output. UD creates an AV circulation using normal saline as an indicator introduced into an extracorporeal loop. Blood ultrasound velocity (1560-1585 m/s) is a function of total blood protein concentration (sums of proteins in plasma and in red blood red cells), temperature, and other factors. Therefore, the injection of saline (having an ultrasound velocity of 1533 m/sec) into the AV loop decreases the overall blood ultrasound velocity, and produce dilution curves. The saline indicator is detected by a venous clamp-on sensor on the AV loop when it is injected, prior to entry into the patient's right heart atrium. As the indicator traverses the heart and lung, a concentration curve in the arterial line is recorded and used in the well known Stewart-Hamilton equation to calculate CO.

Methods to measure CO may further include electrical cardiography, which is similar to ICG (discussed above) in that thoracic electrical bioimpedance (TEB) is measured. However, electrical cardiometry attributes the steep increase of TEB beat-to-beat to the change in orientation of red blood cells.

Still further, Magnetic Resonance Imaging (MRI) may be used to calculate cardiac output. In particular, velocity encoded phase contrast MRI measures flow within vessels and can be used to detect changes in the phase of proton precession. The changes are proportional to the velocity of the movement of those protons through a magnetic field with a known gradient. An MRI scan results in, for each time point in the cardiac cycle, an anatomical image and an image where the signal intensity in each pixel is directly proportional to the through-plane velocity. One can determine the average velocity in a vessel by measuring the average signal intensity of the pixels in the cross section of the vessel, and then multiplying by a known constant. Flow is then calculated by multiplying the mean velocity by the cross-sectional area of the vessel, and is graphed versus time. The area under the flow versus time curve for one cardiac cycle is the stroke volume and the length of the cardiac cycle determines heart rate. Accordingly, CO is being calculated as the product of stroke volume and heart rate.

Referring again to FIG. 2, one or more of the foregoing approaches are used to measure cardiac output values at step 206 of the method as previously noted. Next, per step 208, target values are created based on the multiple CO measurements taken for each subject. In one embodiment, the multitude of CO measurement samples taken for each subject is examined using e.g., regression to the mean to identify an average value. As previously noted, the application of multiple measurement modalities (listed above) leads to minimization of systematic bias components associated with individual methods, and the above-described oversampling leads to minimization of statistical noise. Therefore an accurate value for the cardiac output is determined and set as the target cardiac output value.

Per step 210, a non-linear mathematical model is then determined to link the input vectors to the computed target values. In one embodiment, multidimensional non-linear optimization is used to determine a mathematical model that transforms the physiologic input data into the target cardiac output data in a least-square optimal fashion. Optimization tools such as those manufactured by HighDim GmbH may be utilized in one embodiment to perform the optimization.

The determination of the mathematical model is done by minimizing the following cost function $$J(F) = \sum_{k=1}^{K} \|F(x_k) - t_k\|^2$$

where $F: \mathbb{R}^M \to \mathbb{R}$ is a M-dimensional non-linear function representing the chosen model, $x_k \in \mathbb{R}$ leis a set of K input vectors, $t_k \in \mathbb{R}$ is a set of K target CO values.

An optimal in the sense of the chosen minimization criteria solution is defined as $$\hat{F} = \underset{F}{\mathrm{argmin}}(J(F))$$

The solution can be determined using non-linear optimization methods e.g. Gauss-Newton method.

The mathematical model generated by the method of FIG. 2 may be stored as a computer program executable by one or more devices to which it is distributed or stored on. Exemplary implementations of the model are illustrated at Appendices I and II hereto (which are discussed in greater detail below).

Calculating Cardiac Output Using the Mathematical Model

Figure 3:
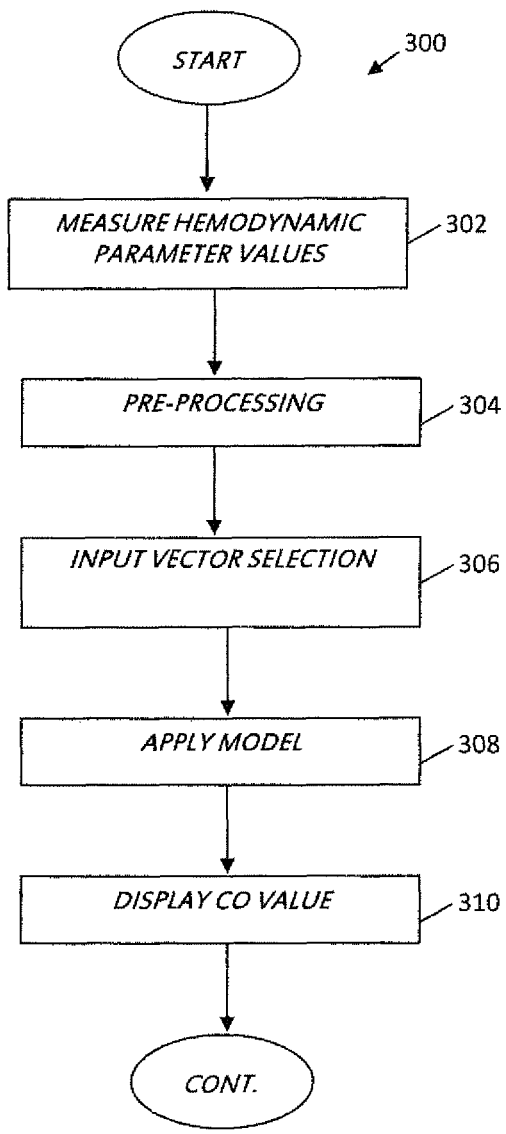
FIG. 3 is a flow diagram illustrating one embodiment of a generalized method for calculating cardiac output given the optimized mathematical model of FIG. 2.

Referring now to FIG. 3, an exemplary method 300 for calculating cardiac output of an individual subject given the mathematical model discussed above (and generated via the method of FIG. 2) is illustrated. As previously discussed, in one embodiment, the mathematical model used for calculating cardiac output is distributed as a software application to a device for applying the method to an individual patient. The operator of the device then performs the steps discussed below.

As shown, per step 302, a plurality of hemodynamic parameters of the individual subject are measured non-invasively using applanation tonometry. The hemodynamic parameters which are measured are the same hemodynamic parameters which were selected at the time the input vector was generated. In other words, the hemodynamic parameters which were measured at step 202 above for the plurality of subjects are the same hemodynamic parameters which are measured for the individual subject at step 302. In one instance, the measured parameters include height, weight, systolic blood pressure (PSys), diastolic blood pressure (PDia), and beat-to-beat interval (BTBI). As noted above, the blood pressure measurements may be obtained via traditional measurement tools, or via more advanced tonometric or even invasive methods (e.g., where an A-line or similar is already installed for other purposes).

Next, per step 304, the measured hemodynamic parameter data is entered into the device running the cardiac output calculation algorithm (such as the device discussed below with respect to FIG. 5), and is pre-processed. In one embodiment, pre-processing of the hemodynamic parameter data includes using the measured data to derive additional parameters. For example, the PSys and PDia measurements may be used to calculate pulse pressure (PP), mean arterial pressure (MAP), and the maximal slope within systole (dPdtMax). Additionally, the measured value of BTBI is used to calculate systolic area (SysA). Pre-processing of the measured data may be performed by the operator manually, by the device for calculating CO (such as that of FIG. 5 discussed below), or by a separate device than the CO calculation device (which may be in communication therewith).

The measured, derived, and entered hemodynamic parameters can be expressed as a vector similar to the vectors generated above with respect to step 204. As noted previously, the hemodynamic and other parameters which are collected regarding the individual subject are in the exemplary embodiment identical to those collected during the model generation (FIG. 2), or at least at a minimum contain the same elements needed for the calculations discussed below. Hence, these may be expressed in a vector similar to those which were generated for the plurality of subjects above. In particular, the vector may be represented as:

$x$=[Gender,Age,Height,Weight,PSys,PDia,PP,BTBI, MAP,dPdtMax,SysA]$^T$

Various ones of specific data points may be detected within the (continuous) bio-signals, and used to enable selection of one of the plurality of input vectors (generated at step 204) which corresponds to the hemodynamic parameters entered for the individual subject (step 306). Alternatively, this step may be omitted and the model may be applied directly to the created vector (corresponding to the individual subject's actual data); see step 308 discussed below.

Next per step 308, the non-linear mathematical model is then employed to correlate the input vector of the individual subject to the computed target values. Appendices I and II illustrate exemplary Matlab-compatible code for applying the cardiac output obtaining parameters for implementation in the algorithm for calculating cardiac output according to the present disclosure. As shown, application of the algorithm involves first calling a plurality of parameters (labeled "params" in Appendices I and II) for entry into the algorithm.

Generally the values within the parameters are constants, which are derived from standard information. The parameters are stored on a storage device in communication with a processor executing the cardiac output algorithm. In one embodiment, the storage device and processor are co-located on a cardiac output calculation apparatus, such as that discussed below with respect to FIG. 5. The data within the "params" is called on for use within the algorithm as shown in Appendix II. Although illustrated as Matlab-compatible code, it is noted that the present disclosure is in no way limited to any particular computing language or software package, the illustrated embodiment is merely exemplary of the functionality of the cardiac output calculation algorithm.

The following pseudo-code describes generally the steps performed by the CO calculation algorithm:
Given the following parameters:
x—input vector [11] composed as:

$$x = [\text{Gender, Age, Height, Weight, PSys, PDia, PP, BTBI, MAP, dPdtMax, SysA}]^T$$

A—matrix [13, 11]; the coefficients of the matrix are given in FIG. 3a
b, w, $x_1$, $x_2$—vectors [13]; the coefficients of the vectors are given in FIG. 3a
alpha, beta, gamma1, gamma2, gamma3—scalars with values given in FIG. 3a
z—auxiliary vector [13]
v—auxiliary scalar Using the abstraction of matrix and vector algebra, cardiac output is computed according to the non-linear mathematical model as follows:

$z=(x-x_1)\cdot{}^*x_2+\text{beta}$; % element-wise vector multiplication $t=A^*z+b$; % matrix-vector multiplication $t=2\cdot/(1+\exp(-2^*t))-1$; % element-wise evaluation of a non-linear function $v=w^T{}^*t+\text{alpha}$; % inner product $SV=(v-\text{gamma1})^*\text{gamma2}+\text{gamma3}$; % stroke volume in mL $CO=(60/1000)^*SV/BTBI$; % cardiac output in L/min Therefore, upon entry of the vector data of an individual subject, the data is compared to previously obtained data via a series of mathematic steps to arrive at stroke volume, which is used in conjunction with the BTBI to arrive at an accurate measure of cardiac output. It is further recognized that the individual living subject need only have certain hemodynamic parameters measured, and the measured parameters are ideally measured non-invasively. Thus, the apparatus and methods discussed herein provide an effective, accurate and non-invasive mechanism for calculating cardiac output of a living subject.

The cardiac output value is then displayed or otherwise provided to a user (per step 310). In one embodiment, this occurs when an apparatus for calculating CO delivers the CO value to a display device. Alternatively, the CO calculation device may be configured to include a display which directly displays the value derived by the algorithm. the determined CO (or any constituent data associated therewith) may also be provided to an input of another device or process, such as one which utilizes CO in further evaluation (e.g., multiparameter analysis) of a subject. See e.g., U.S. Pat. No. 6,705,990 issued Mar. 16, 2004 and entitled "Method and apparatus for monitoring physiologic parameters of a living subject", which is incorporated herein by reference in its entirety.

Cardiac Output Calculation Algorithm Derivation Device

As noted above, the algorithm for calculating cardiac output is generated by a device configured to receive a plurality of data from a plurality of test subjects. The exemplary embodiment of the device 400 (see FIG. 4) uses the received information to correlate hemodynamic data to cardiac output via a non-linear optimization method.

As shown, the device 400 generally comprises an interface 404, storage entity 406, and processor 402. The processor 402 is configured to run at least a data derivation application 410, an input vector generation application 412, a parameter generation application 414, and an algorithm derivation application 416. It will be appreciated that while the foregoing are described herein as essentially separate applications or modules, they may also be partly or wholly combined with one another (and/or yet other routines or modules) depending on the particular implementation. They may also be distributed across two or more physical and/or software environments, including separate devices disposed at separate locations (which may include e.g., "cloud" based processes).

The data derivation application 410 comprises a plurality of instructions which are configured to utilize information entered via the user input 420 or data interface 404 to derive other data. For example, the systolic and diastolic blood pressure measurements may be used to derive a value for pulse pressure (PP, measured in mmHg), a mean arterial pressure (MAP, in mmHg/s), a maximal slope within a systole (dPdtMax, measured in mmHg/s), and a systolic area (SysA, measured in mmHg*s). The mathematical processes needed to derive each of these values are discussed above and, according to the present embodiment, are performed by the data derivation application 410. Hence, an operator of the device upon entry of the measured hemodynamic parameter data via an input device 420 (or via another data source, such as received via the data interface 404 or a wireless interface, not shown), need merely run the data derivation application 410 to obtain the foregoing values, which may be displayed at a display device 422 in communication with the device 400.

The input vector generation application 412 comprises a plurality of instructions which are configured to generate a plurality of vectors based at least in part on the measured hemodynamic parameters, entered data (such as age and gender), and data derived from the measured hemodynamic parameters (such as via the data derivation application 410 discussed above). Each vector corresponds to individual ones of the plurality of test subjects. The vectors, in one embodiment, comprise a matrix or "tuple" as illustrated below:

$$x=[\text{Gender,Age,Height,Weight,PSys,PDia,PP,BTBI,MAP,dPdtMax,SysA}]^T$$

The parameter generation application 414 comprises a plurality of instructions which are configured to generate a plurality of matrixes (or "params" as referred to in Appendices I and II) having coefficients implemented in the algorithm for calculating cardiac output according to the present disclosure. The values within the parameters are constant values derived from standard information. The parameters are stored on a storage entity of an apparatus which will perform the cardiac output calculation algorithm (such as the apparatus of FIG. 5 discussed below).

The algorithm derivation application 416 comprises a plurality of instructions which are configured to generate a cardiac output calculation algorithm based at least in part on the input vectors and the parameters. In one embodiment, the cardiac output calculation algorithm comprises a plurality of steps as illustrated in Appendices I and II discussed above.

Once the algorithm is generated, it is transferred to a device operated by a clinician which will be used to calculate cardiac output of an individual subject (i.e., a patient). The device may for example be that described with respect to FIG. 5 below.

It will be appreciated that while the input and display devices 420, 422 are illustrated as separate components, the foregoing may be integrated into a single device (such as via e.g., a capacitive or other touch-screen device of the type well known in the art). Moreover, the apparatus 400 of FIG. 4 may take on literally any form factor, such as a fixed or desktop device, a mobile wireless device (e.g., tablet computer), a card or "blade" for use in a larger host device, etc.

Cardiac Output Calculation Device

Figure 5:
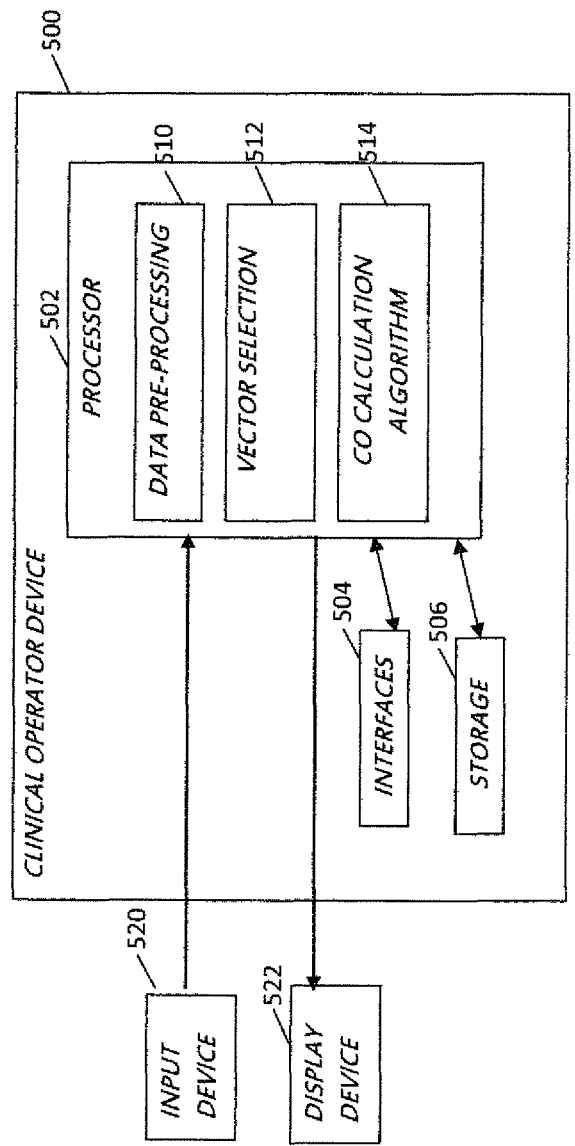
FIG. 5 is a block diagram illustrating one exemplary embodiment of an apparatus for calculating cardiac output according to the present disclosure.

As noted above, the algorithm for calculating cardiac output is in the exemplary embodiment implemented by clinician-operated device. The device is configured to receive a plurality of data specific to an individual patient (i.e., hemodynamic data and other entered data) to calculate cardiac output of the subject. In one embodiment, the device 500 of FIG. 5, is utilized for these functions.

As shown, the exemplary device 500 generally comprises a data interface 504, storage entity 506, and processor 502. The processor 502 is configured to run at least a data pre-processing application 510, a vector selection application 412, and the CO calculation algorithm 514.

The data pre-processing application 510 comprises a plurality of instructions configured to utilize information entered via the input device or via the data interface 504 to derive data needed for calculating CO. In one example, measurements for systolic and diastolic blood pressure of the patient are entered by a clinician via an input device 520. The pre-processing application 510 uses this input to calculate e.g., pulse pressure, a mean arterial pressure, a maximal slope within a systole, and a systolic as previously described.

In one variant, the vector selection application 412 comprises a plurality of instructions configured to select a vector from among the plurality of vectors generated with respect to the test subjects. However, it is appreciated that this application 412 may be omitted in one embodiment.

The CO calculation algorithm 514 comprises a plurality of instructions configured to apply the CO calculation algorithm to the data regarding the individual subject. In one embodiment, the algorithm generally comprises the steps indicated in the exemplary code expressed in Appendices I and II hereto. Once the CO is calculated, it is displayed to a user of the device 500 via a display device 522 in communication therewith, or otherwise output (e.g., via the data interface 504, or via another interface such as a Wi-Fi or similar wireless interface, not shown).

Figure 4:
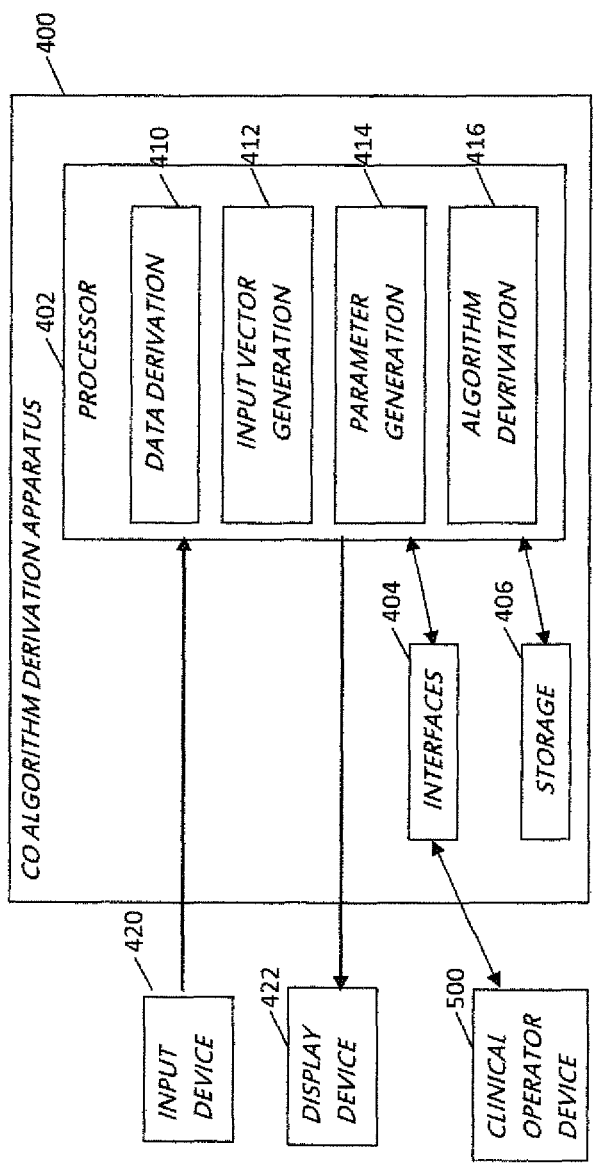
FIG. 4 is a block diagram illustrating one exemplary embodiment of an apparatus for generating an algorithm to compute cardiac output according to the present disclosure.

As with the device of FIG. 4, it will be appreciated that while the foregoing are described herein as essentially separate applications or modules, they may also be partly or wholly combined with one another (and/or yet other routines or modules) depending on the particular implementation. They may also be distributed across two or more physical and/or software environments, including separate devices disposed at separate locations (which may include e.g., "cloud" based processes).

Moreover, while the input and display devices 520, 522 are illustrated as separate components, the foregoing may be integrated into a single device (such as via e.g., a capacitive or other touch-screen device of the type well known in the art).

Further, the apparatus 500 of FIG. 5 may take on literally any form factor, such as a fixed or desktop device, a mobile wireless device (e.g., tablet computer), a card or "blade" for use in a larger host device, etc.

It will also be recognized that the devices 400, 500 of FIGS. 4 and 5, respectively, may be combined with one another so as to comprise a substantially unitary form factor.

Other Applications

The algorithm discussed herein may be further configured to compute other hemodynamic parameters. For example, pulse pressure variation (PPV) and stroke volume variation (SVV) may be calculated based on stroke value (SV) samples which can be computed for every BP beat using the CO calculation algorithm. As noted above, pulse pressure (PP) is calculated based on the known values of systolic and diastolic pressure. As is indicated in the example code given at Appendices I and II, stroke volume (SV) is also calculated using the apparatus and methods disclosed herein.

Hence, PPV and SVV may be calculated as follows:

$$PPV=100(PP_{max}-PP_{min})/PP_{med}$$

$$SVV=100(SV_{max}-SV_{min})/SV_{med}$$

where $PP_{max}$ is the median of four maximal PP samples collected over the last 30 seconds, $PP_{min}$ is the median of four minimal PP samples collected over the last 30 seconds, $PP_{med}$ is the median of the PP samples collected over the last 30 seconds. In the same way $SV_{min}$ is the median of four maximal SV samples collected over the last 30 seconds, $SV_{min}$ is the median of four minimal SV samples collected over the last 30 seconds, $SV_{med}$ is the median of SV samples collected over the last 30 seconds. This type of computation allows estimation of the average variation of PP and SV during several respiratory cycles within 30 seconds. This and other hemodynamic parameter calculations may be accurately made using the methods and apparatus discussed herein.

It is noted that many variations of the methods described above may be utilized consistent with the present disclosure. Specifically, certain steps are optional and may be performed or deleted as desired. Similarly, other steps (such as additional data sampling, processing, filtration, calibration, or mathematical analysis for example) may be added to the foregoing embodiments. Additionally, the order of performance of certain steps may be permuted, or performed in parallel (or series) if desired. Hence, the foregoing embodiments are merely illustrative of the broader methods of the disclosure disclosed herein.

While the above detailed description has shown, described, and pointed out novel features of the disclosure as applied to various embodiments, it will be understood that various omissions, substitutions, and changes in the form and details of the device or process illustrated may be made by those skilled in the art without departing from the spirit of the disclosure. The foregoing description is of the best mode presently contemplated of carrying out the disclosure. This description is in no way meant to be limiting, but rather should be taken as illustrative of the general principles of the disclosure. The scope of the disclosure should be determined with reference to the claims.

APPENDIX I

```
%  Get parameters of the algorithm for CO estimation
%
%  INPUT: none
%
%  OUTPUT:
%      params - record with parameters used for computing CO in
COAlgorithm
%
function params = GetCOAlgorithmParams( )
% each line represents a row of the matrix A
params.A = [
    -0.1533488  0.3432636  0.2303996  0.0799955  0.9942184  1.0516741  1.4017904
0.7221999  -1.0707682  -0.7403769  0.3655542
    -2.1420436  0.2307725  31.9536575  -17.0511377  -23.6180292  -53.9350695  39.1095514  -
1.9651923  18.2812083  27.0095096  -26.4150195
    -1.3416001  0.4927524  -6.3081827  1.6230446  1.8639998  5.8535480  -5.9814890
0.6574029  -8.2174556  9.9503078  0.7112309
    0.1697857  -0.2748877  -0.0025648  -0.0667792  -1.4308995  -0.6776958  -1.2546391  -
1.0270306  1.1775402  0.6487826  0.5594860
    -0.1905015  0.6216697  0.7289633  -0.8130879  1.1220655  1.0800732  -0.9301936
3.9137556  -1.7288043  -3.2216023  -1.5368572
    0.6148384  -1.3319874  -4.2851305  0.8804270  2.5862243  2.1720434  -0.3209328  -
2.9214513  -0.2793806  3.7305908  -4.2374031
    -0.1104034  -3.4360560  -0.2962635  0.7923516  3.0327965  2.1058205  0.6166110
0.9706389  -3.5641664  -0.1689592  -1.8669218
    -4.6420576  1.7617996  2.7452949  3.1980180  0.8219553  1.7432793  0.1672287  -
3.1503848  -0.1401345  -2.6184968  3.6598161
    0.1285111  -0.7833867  -0.5418184  0.4876557  -1.1651051  -1.6888112  0.6939426
0.1097354  0.6012888  -0.1718374  0.0104232
    -0.0270592  -0.1844995  0.5767859  0.0230415  0.5888197  0.2527552  -0.0625127
0.0084564  -0.3063109  0.0007053  0.3143907
    2.1696144  0.5864078  13.2248019  -1.2360316  5.3271783  7.8097896  -4.7231150  -
5.1923772  -11.2512895  -7.7326881  17.1223962
    -0.0816308  0.4976947  -0.9733797  -1.2464292  2.3902057  0.6314297  2.8902649
1.3992242  -2.1201249  -1.5334230  -1.6967440
    -0.0674949  -0.0488421  0.8281057  -0.1106215  0.9414756  0.3599624  -0.2377854  -
0.0187493  -0.4027902  0.0225384  0.4579490
    ];
params.b = [2.2912304  -1.3304566  5.5784743  -1.6354139  2.4464477
2.7843510  -2.5799514  -0.1497923  -0.5888276  -0.9936822  5.9496294
0.5663329  -1.0682231]';
params.w = [1.5965523  -0.0045069  0.0348864  1.6816569  -0.0357161
0.0348668  -0.1104636  0.0353734  0.4026207  5.1423459  -0.0253799
0.2279914  -2.9787380]';
params.alpha = 1.1596881;
params.x1 = [0.0000000  18.0000000  120.0000000  40.0000000  44.2452469
13.9165134  7.8926964  0.3950617  29.8284321  89.0000000  1.2545718]';
params.x2 = [2.0000000  0.0217391  0.0172414  0.0153846  0.0104386
0.0122365  0.0176343  1.7142857  0.0119482  0.0008602  0.0736006]';
params.beta = -1.0000000;
params.gamma1 = -1.0000000;
params.gamma2 = 116.5000000;
params.gamma3 = 0.0000000;
```

APPENDIX II

```
%
%  Algorithm for estimation of Cardiac output
%
%  INPUT:
%      x - input vector of size [11] which is composed as
%      x =
[Gender,Age,Height,Weight,PSys,PDia,PP,BTBI,MAP,dPdtMax,SysA]'
%      where
%          Gender - 0 for female, 1 for male
%          Age - age, years
%          Height - height, cm
%          Weight - weight, kg
%          PSys - systolic pressure, mmHg
%          PDia - diastolic pressure, mmHg
%          PP - pulse pressure, mmHg
%          BTBI - interval from the current beat to the previous beat, s
%          MAP - mean arterial pressure, mmHg
%          dPdtMax - maximal slope within systole, mmHg/sec
%          SysA - systolic area, mmHg*s
%
%      params - parameters of the algorithm (see GetCOAlgorithmParams)
```

APPENDIX II-continued

```
%
%  OUTPUT:
%      CO - cardiac output, lpm
%
function CO = COAlgorithm(x, params)
xx = x - params.x1; % vector subtraction
xx = xx .* params.x2; % elementwise vector multiplication
xx = xx + params.beta;
t = params.A * xx; % matrix-vector multiplication
t = t + params.b; % vector addition
t = 2./(1 + exp(-2*t))-1; % elementwise evaluation
v = sum(params.w .* t); % inner product
v = v + params.alpha;
v = (v - params.gamma1) .* params.gamma2 + params.gamma3;
CO = (60/1000)*v/x(8);
end
```

What is claimed is:

1. A method of computing cardiac output (CO) of a living subject, comprising:

obtaining a plurality of target CO values;
generating an mathematical model based at least in part on said target CO values;
obtaining a plurality of physiologic input source data from said living subject;
transforming said plurality of physiologic input source data using at least said mathematical model; and
expressing a result of said transformation as a CO value in physiologic units.

2. The method of claim 1, wherein said target CO values are obtained by performing at least one of:
waveform-based methods;
Doppler echocardiography-based methods; or
thermodilution-based methods.

3. The method of claim 1, wherein said optimization module comprises a multi-dimensional non-linear optimization algorithm.

4. The method of claim 1, wherein said plurality of physiologic input source data comprises at least one of:
systolic pressure of said living subject;
diastolic pressure of said living subject; and
pulse pressure of said living subject.

5. The method of claim 1, wherein said plurality of physiologic input source data comprises at least one of:
beat-to-beat interval;
mean arterial pressure;
maximal slope of pressure rise during systole; and
area under a systolic portion of a pulse pressure wave.

6. The method of claim 1, wherein said plurality of physiologic input source data comprises at least one of:
age of said living subject;
gender of said living subject;
height of said living subject; and
weight of said living subject.

7. The method of claim 1, wherein said act of transforming comprises fitting said physiologic input data into said target CO data in a least-square optimal fashion.

8. A non-transitory computer readable apparatus configured to store at least one computer program thereon, said at least one computer program comprising a plurality of instructions which are configured to, when executed by a processing apparatus:
receive a plurality of first data, individual ones of said plurality of first data each comprising cardiac output (CO) values representative of living subjects having a respective plurality of physiologic parameters;
generate a mathematical model to correlate said plurality of CO values to said respective plurality of physiologic parameters;
receive second data, said second data comprising one or more measured physiologic parameters of a particular living subject;
link, in a mathematically optimal way, said second data to one of said plurality of CO values via at least:
detection of one or more specific data points within continuous biosignals received from said particular living subject;
selection of a data vector representative of said continuous bio-signals based at least in part on said detected one or more specific data points; and
application of a mathematical transformation to said selected data vector to arrive at said one of said plurality of CO values; and cause a display of said one of said plurality of CO values.

9. The apparatus of claim 8, wherein said plurality of instructions are further configured to process said one or more measured physiologic parameters to a format which a physiologic parameter of said first data is expressed.

10. The apparatus of claim 9, wherein:
said format said first data is expressed as comprises pulse pressure variation;
said second data comprises pulse pressure of said particular living subject; and
said plurality of instructions configured to process do so via estimation of an average pulse pressure of said particular living subject over one or more respiratory cycles.

11. The apparatus of claim 9, wherein said format said first data is expressed as comprises stroke volume variation;
said second data comprises stroke volume of said particular living subject; and
said plurality of instructions configured to process do so via estimation of an average stroke volume of said particular living subject over one or more respiratory cycles.

12. A computer readable apparatus comprising a storage medium configured to store at least one computer program thereon, said at least one computer program comprising a plurality of instructions which are configured to, when executed by a processing apparatus:
receive a plurality of first data, each of said plurality of first data comprising at least one cardiac output (CO) value representative of living subjects having a respective plurality of physiologic parameters;
generate a mathematical model to correlate said at least one CO value to said respective plurality of physiologic parameters for at least a portion of living subjects;
receive second data, said second data comprising one or more measured physiologic parameters of a particular living subject;
link, in a mathematically optimal way, said second data to said at least one of said plurality of CO values via at least:
detection of one or more specific data points within continuous bio-signals received from said particular living subject;
selection of a data vector representative of said continuous bio-signals based at least in part on said detected one or more specific data points; and
application of a mathematical operation on said selected data vector to arrive at said at least one CO value; and
cause presentation of said at least one CO value.

13. A method of computing cardiac output (CO) of a living subject, comprising:
obtaining a plurality of target CO values;
generating an mathematical model based at least in part on said target CO values;
obtaining a plurality of physiologic input source data from said living subject;
transforming said plurality of physiologic input source data using at least said mathematical model, said transforming comprising multidimensional non-linear optimization; and
expressing a result of said transformation as a CO value in physiologic units.

* * * * *